US010028882B1

(12) United States Patent
Ross

(10) Patent No.: US 10,028,882 B1
(45) Date of Patent: Jul. 24, 2018

(54) SEXUAL STIMULATION DEVICE CONTAINING A RIDE CONTROL RING

(71) Applicant: Justin Ross, Beverly Hills, CA (US)

(72) Inventor: Justin Ross, Beverly Hills, CA (US)

(73) Assignee: Pacific Coast Holdings IP, LLC, Torrance, CA (US)

( * ) Notice: Subject to any disclaimer, the term of this patent is extended or adjusted under 35 U.S.C. 154(b) by 190 days.

(21) Appl. No.: 14/948,014

(22) Filed: Nov. 20, 2015

(51) Int. Cl.
*A61F 5/00* (2006.01)
*A61H 19/00* (2006.01)
*A61H 23/02* (2006.01)

(52) U.S. Cl.
CPC ............ *A61H 19/32* (2013.01); *A61H 23/02* (2013.01); *A61H 2201/169* (2013.01)

(58) Field of Classification Search
CPC ........ A61H 19/50; A61H 19/40; A61H 19/34; A61H 23/02; A61H 19/32
USPC ...................................................... 600/38–41
See application file for complete search history.

(56) References Cited

U.S. PATENT DOCUMENTS 7,658,707 B2 * 2/2010 Topolev ................. A61H 19/34 600/38
7,678,042 B2 * 3/2010 Jackson .................... A61F 5/41 600/41
2007/0038019 A1 * 2/2007 Weng ........................ A61F 5/41 600/38
2013/0296645 A1 * 11/2013 Evans .................... A61H 19/50 600/41
2015/0148720 A1 * 5/2015 Harmon ................. A61H 19/30 601/70

* cited by examiner

*Primary Examiner* — Samuel Gilbert
(74) *Attorney, Agent, or Firm* — Thomas I. Rozsa

(57) ABSTRACT

A sexual stimulation device which contains a vibrating member or vertical bullet which is attached at opposite ends to two elastic rings which may be of similar size or different sizes. The top ring is designed to have the index finger inserted inside the ring. The bottom ring is designed to have a male's penis and testicles fit inside of the ring. The device is battery operated and is primarily intended to be used for external stimulation which includes a vertical bullet (also referred to as a vibration motor) having a flexible bottom ring that attaches around a male sexual organ and can be positioned by pulling the top ring. The vertical bullet vibrates at different speeds and pulses to create different stimulations against sexual organs.

10 Claims, 9 Drawing Sheets

SEXUAL STIMULATION DEVICE CONTAINING A RIDE CONTROL RING

BACKGROUND OF THE INVENTION

1. Field of the Invention

The present invention relates to the field of physical (as opposed to medical pills, liquids, etc.) sexual enhancement products.

2. Description of the Prior Art

While sexual stimulation devices have been in existence for many years, the present inventor is unaware of any sexual stimulation device which performs the unique features of the present invention.

SUMMARY OF THE INVENTION

The present invention relates to the field of physical sexual stimulation and sexual enhancement devices which are used for external sexual enhancement by providing a sexual partner (primarily, but not exclusively, female) control over the other sexual partner's penis. The present invention also provides stimulation of sexual organs to provide pleasure by creating a vibrational effect against the sexual organs to provide stimulation and sexual enhancement.

The present invention is a sexual stimulation device which contains a vibrating member or vertical bullet which is attached at opposite ends to two elastic rings which may be of similar size or different sizes. The top ring is designed to have the index finger inserted inside the ring. The bottom ring is designed to have a male's penis and testicles fit inside of the ring.

It is an object of the present invention to provide a battery operated sexual stimulator for external stimulation which includes a vertical bullet (also referred to as a vibration motor) having a flexible bottom ring that attaches around a male sexual organ and can be positioned by pulling the top ring. The vertical bullet vibrates at different speeds and pulses to create different stimulations against sexual organs.

It is another object of the present invention to create a vibrational stimulation device which has a bottom ring that will stretch comfortably around the male organ and testicles but remain in place while in use.

It is another object of the present invention to provide a sexual stimulation device with a top ring that allows a user to adjust the location of the vertical bullet while in use.

It is another object of the present invention to provide a sexual stimulation device to allow the user to control the speed of the vibration or pulsation and location of the vertical bullet.

It is a further object of the present invention to provide a sexual stimulation device to allow the user to easily control the location of the vertical bullet by using one finger.

It is an additional object of the present invention to be able to use the sexual stimulation device internally, as well as externally, in a safe manner.

Further novel features and other objects of the present invention will become apparent from the following detailed description and discussion.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

Figure 1:
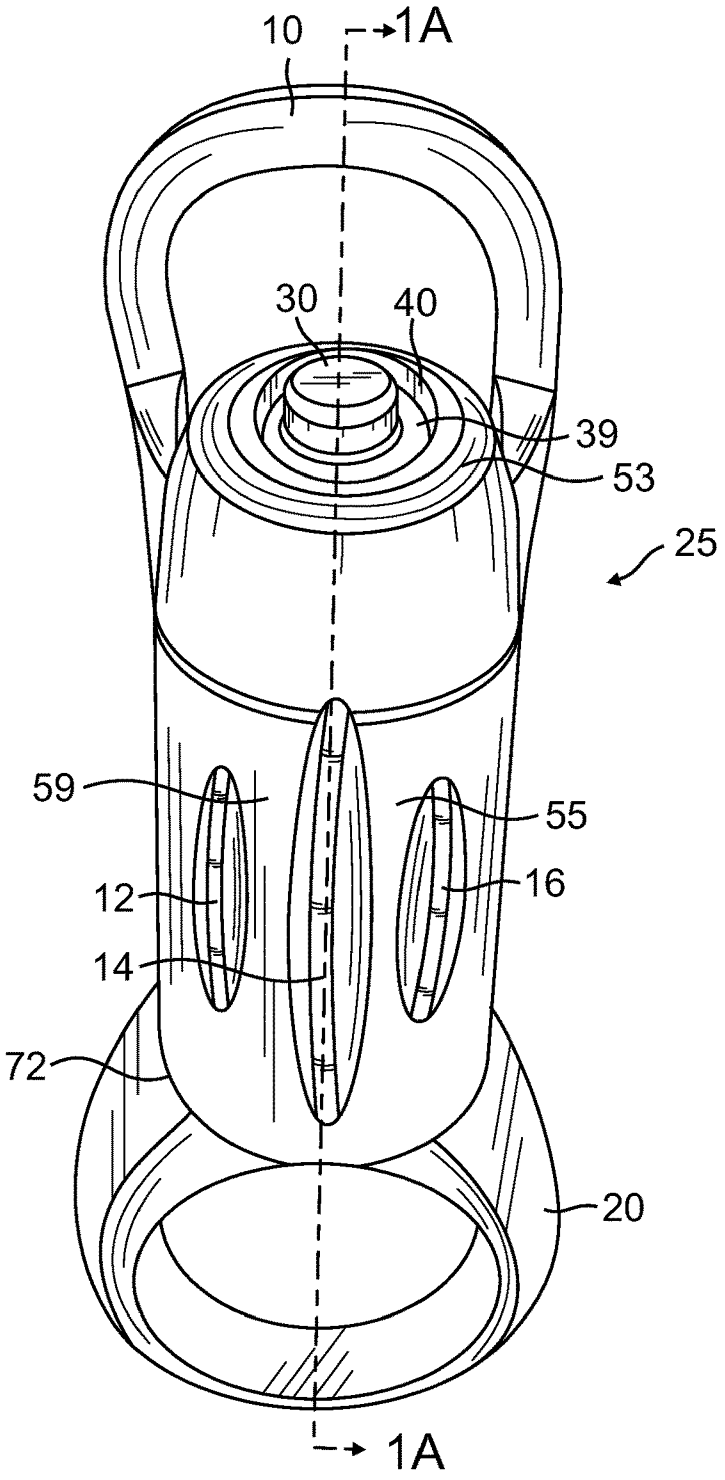
FIG. 1 is a front elevational view of the present invention.
Figure 1A:
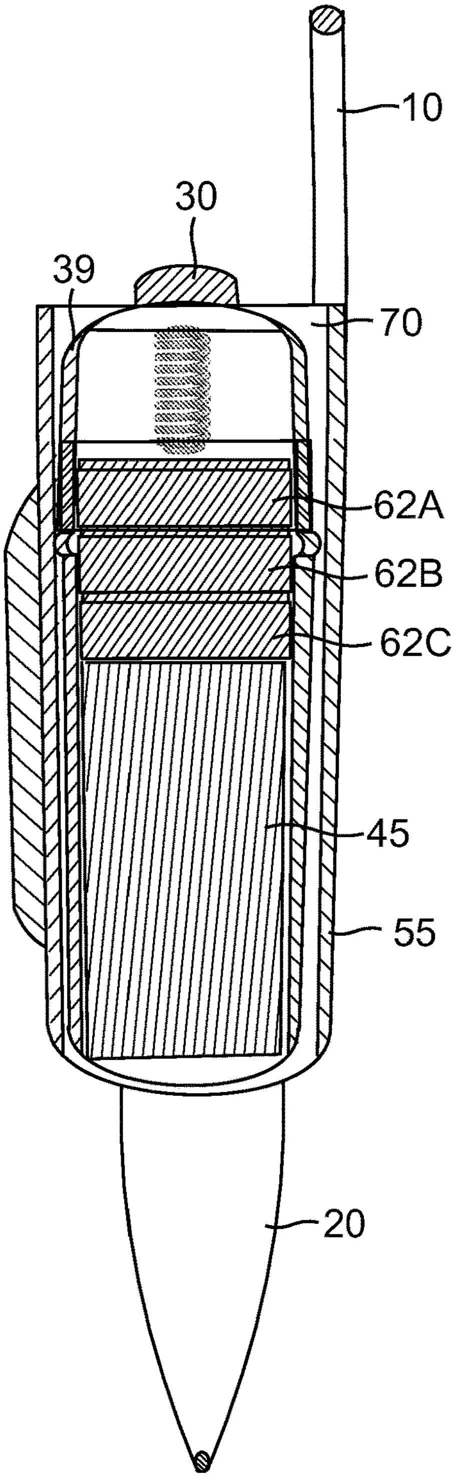
FIG. 1A is a cross-sectional view taken along line 1A-1A of FIG. 1.
Figure 2:
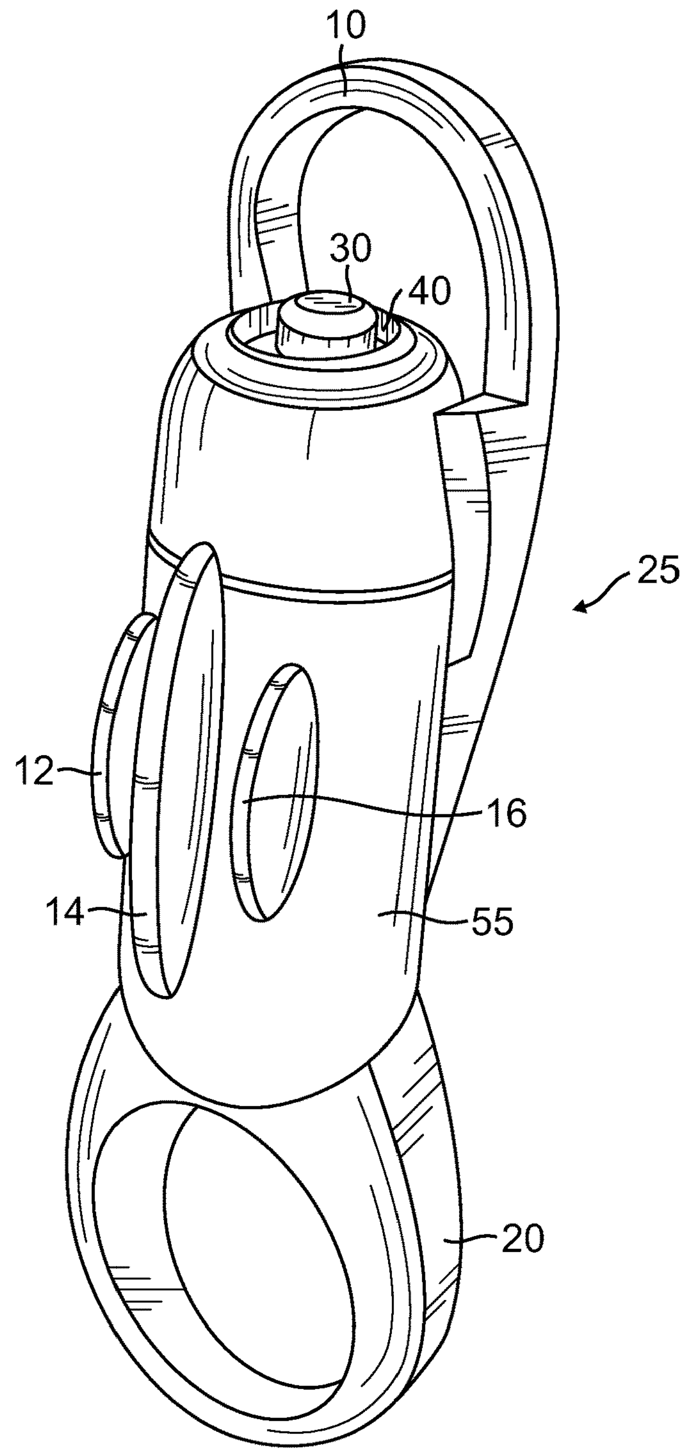
FIG. 2 is a front-side perspective view of the present invention taken from the view illustrated in FIG. 1, and rotated through a vertical clockwise rotation to illustrate relative positions of front and rear components of the present invention.
Figure 3:
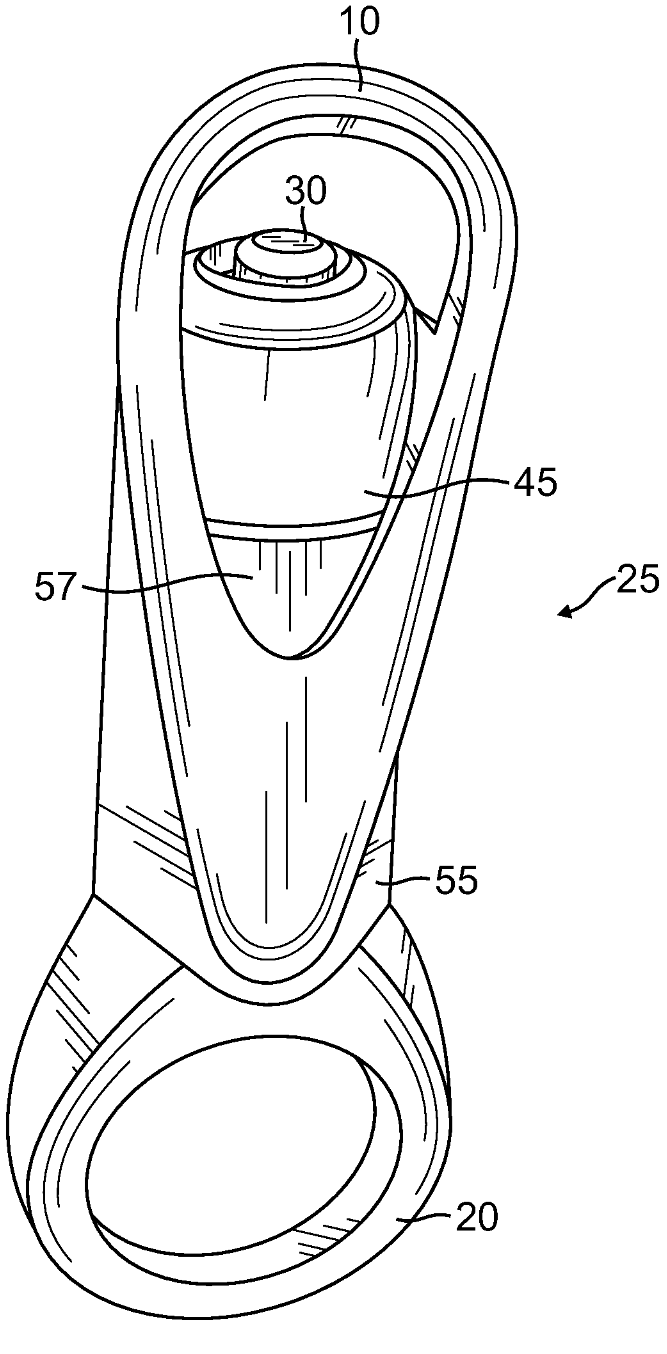
FIG. 3 is a rear-side perspective view of the present invention illustrated from an opposite side of the present invention relative to the view in FIG. 3.

The present invention is a sexual stimulation device to primarily provide external sexual stimulation although, if carefully used, it can also provide internal sexual stimulation. Referring to FIGS. 1, 1A, 2 and 3, there is illustrated the present invention Vibrating control ring 25 which on the rear exterior surface 57 of main housing member 55 retains an upper ring or finger insertion member 10 which allows the user to be able to position exterior sensation ridges 12, 14, and 16 located on the front of exterior surface 59 of main housing member 55 of vibrating control ring 25 to a desired location, primarily on a penis. There is also a lower ring or penis encircling and, if desired, testicles encircling stretchable ring 20 located and retained on at least a portion of second end 72 of main housing member 55, which lower ring is designed to stretch around a male's penis and testicles. As illustrated in the cross-sectional view of FIG. 1A, in addition to FIGS. 1, 2 and 3, the central housing member 55 retains the upper or finger insertion member 10 on an exterior rear surface 57 of main housing member 55 as illustrated in FIGS. 2 and 3.

Referring to FIGS. 1, 1A, 2 and 3, the first end 53 of main housing member 55 has an exterior opening 39 leading to an interior chamber 70 retaining the vertical bullet or vibration member 45. The vibration member 45 includes an on-off and vibration selection button 30 extending out of opening 39 which is surrounded by exterior circumferential wall 40.

Figure 4:
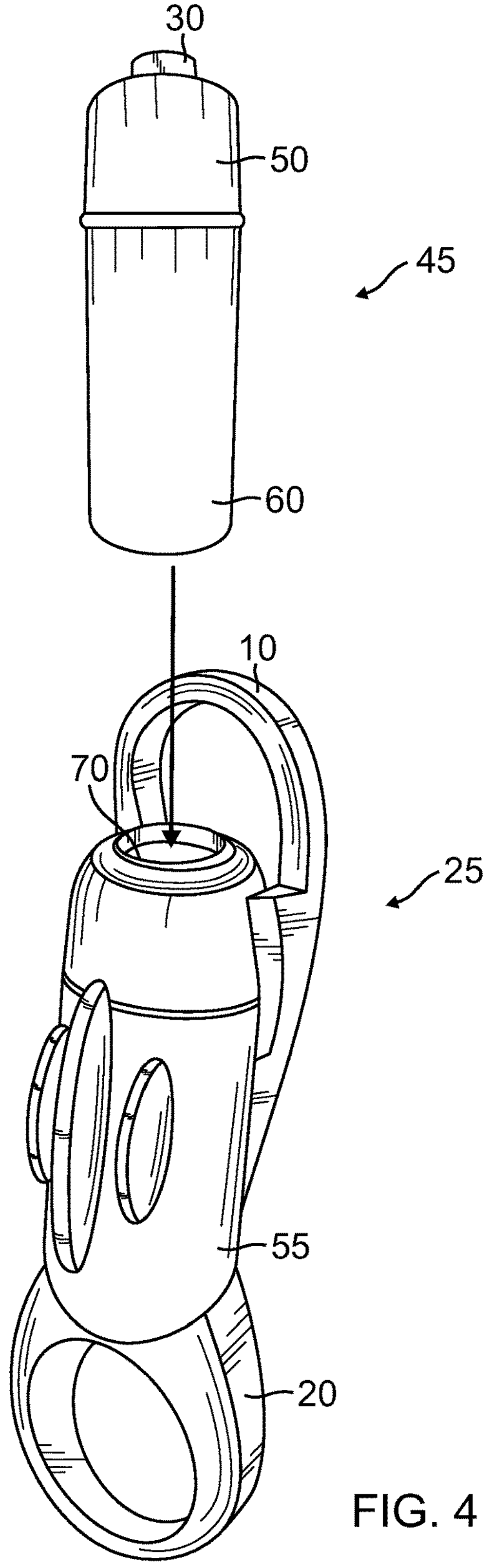
FIG. 4 is an exploded front-side perspective view of the present invention taken from the view illustrated in FIG. 2, the exploded front perspective view with the vertical bullet separated from ride control ring.
Figure 5A:
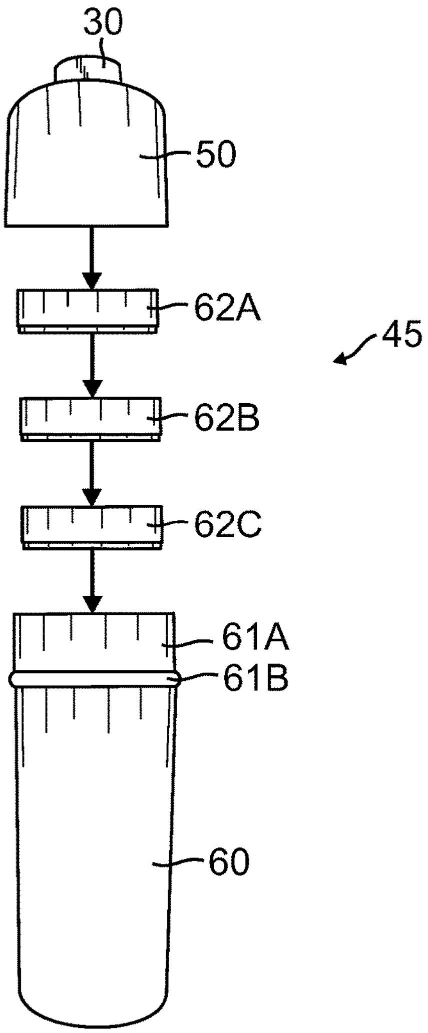
FIG. 5A is an exploded view of the bullet and its component.
Figure 5B:
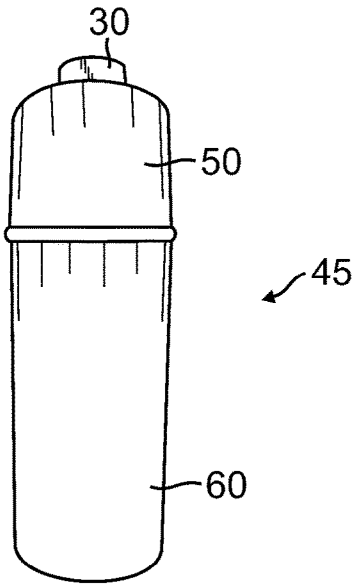
FIG. 5B is a frontal view of the vertical bullet.

Referring to FIG. 4, the vertical bullet interchangeably referred to as vibration member 45 is illustrated removed from the interior chamber 70. The vibration member 45 has an exterior bottom section 60 removably affixed to a top section 50 through which activation button 30 extends. As illustrated in FIGS. 5A and 5B, the vibration member 45 is separated into two major components; an internal battery operated vibration member powered by batteries such as 62A, 62B and 62C and exterior vibration member housing having an upper section 50 that fits over and closes on top of lower section 60. Referring to FIG. 5A, there is illustrated an exploded view of vibration member 45. Upper section 50 fits over reduced diameter section 61A and is stopped by circumferential stopper ring 61B on lower bullet section 60. Vibration member 45 is powered by a multiplicity of batteries 62A, 62B and 62C respectively retained in the interior chambers of bottom section 60 or top section 50. The uppermost battery is in contact with the button 30. The vibration member 45 is retained in interior chamber 70 and transmits vibrational forces to housing 55.

The vibration member 45 is retained within interior chamber 70 of the exterior housing 55 which is made of material selected from the group consisting of rubber, silicone, and flexible soft and strong rubberized material.

When top section 50 is closed around bottom section 60, the connection between the standard upper circuitry (not shown), batteries 62A, 62B and 62C and standard lower circuitry (not shown) is completed. This allows vibration member 45 to be powered on.

The desired speed for the sexual stimulation device 25 is chosen by depressing power button 30 located on top of upper section 50. Depressing power button 30 once yields the lowest vibrating speed. Depressing power button 30 twice yields the second lowest vibrating speed. Depressing power button 30 three times yields the highest vibrating speed. Depressing power button 30 four times pulsates the vibration member 45. Depressing power button 30 five times turns the power to 25 off.

Figure 6:
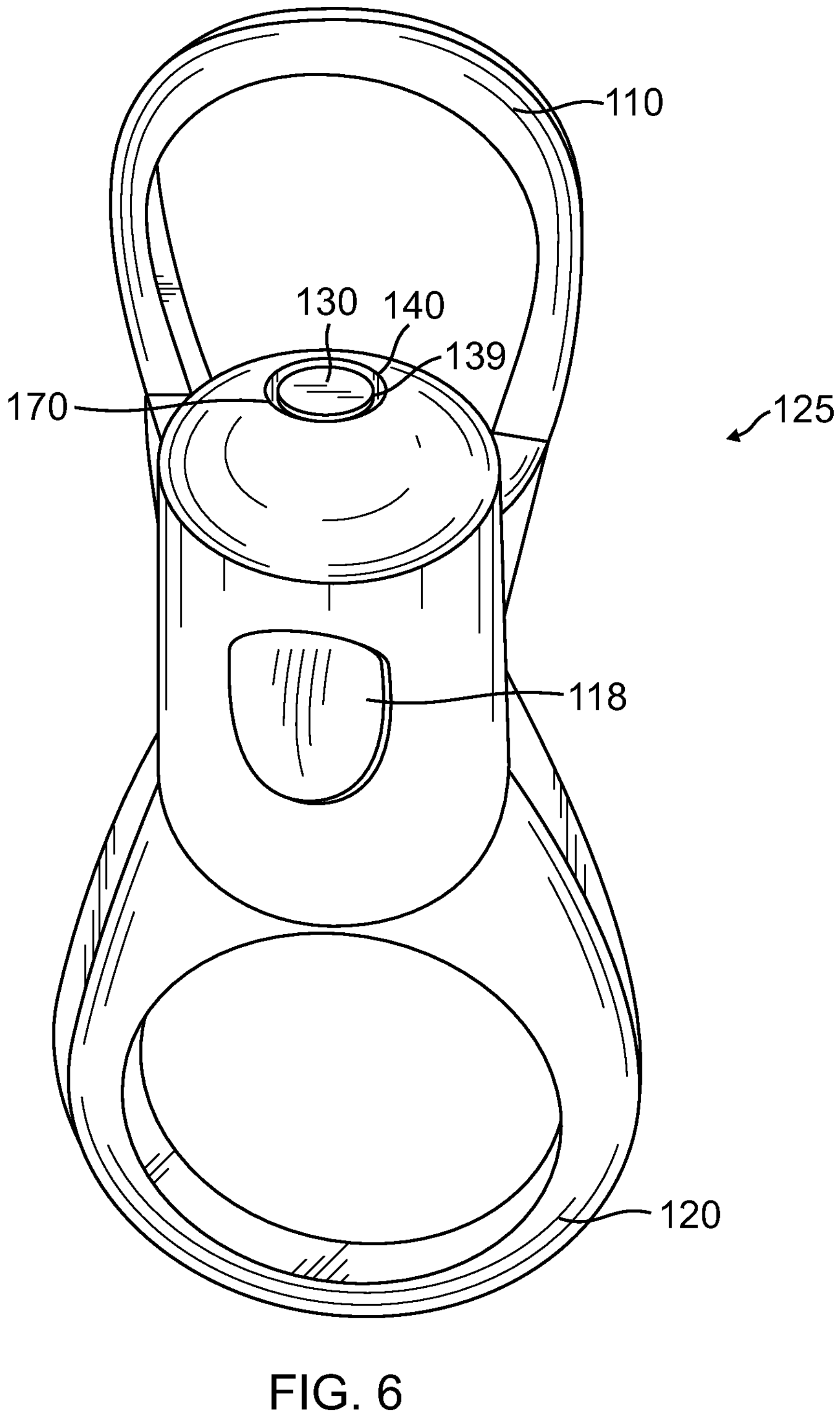
FIG. 6 is a front-side perspective view of an alternative or second embodiment the present invention.
Figure 7:
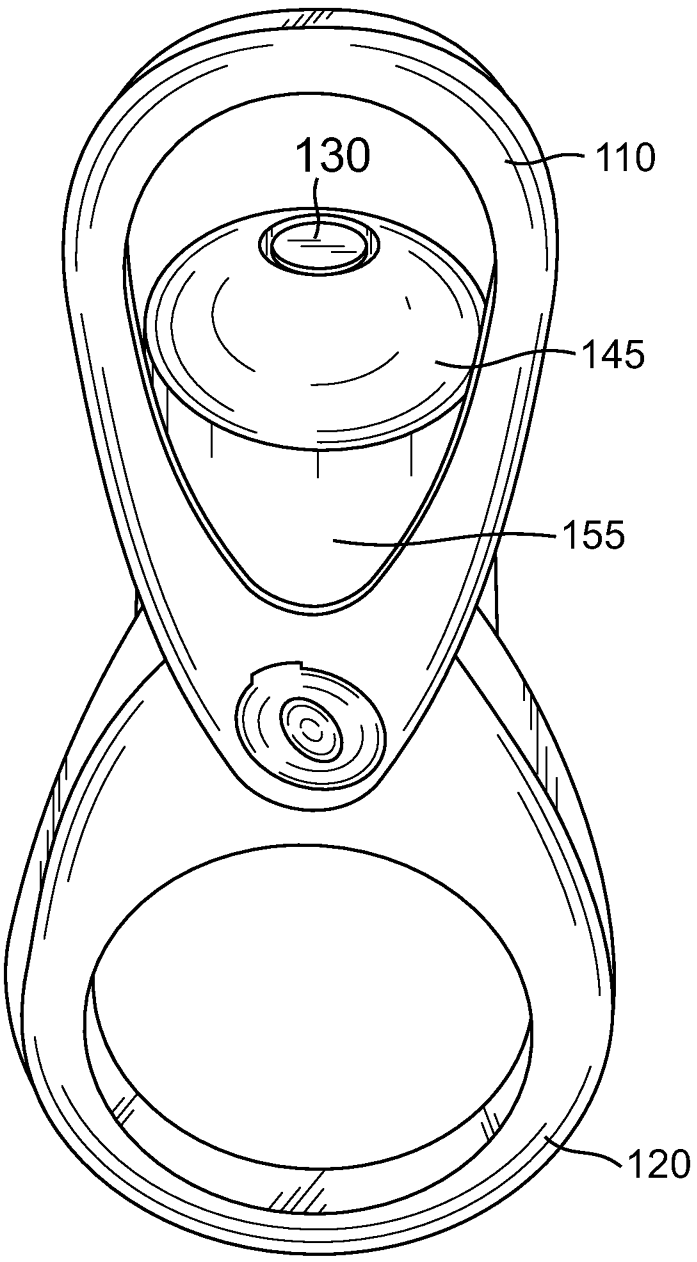
FIG. 7 is a rear-side perspective view of the alternative or second embodiment of the present invention taken from a side opposite to the side illustrated in FIG. 6.

Referring to FIGS. 6 and 7, there is illustrated a second embodiment of the sexual stimulation device vibrating control ring 125. Corresponding parts to the first embodiment are numbered with 100 added to the corresponding number. Similar to the first embodiment, in the second embodiment there is an upper ring 110, a lower ring 120, but only one central ridge 118, and an opening 139 surrounded by circumferential wall 140 and leading to a vibration member housing chamber 170. The second embodiment has a smaller vibration member 145. The power button 130 for vibration member 145 and the speeds for the vibration member 145 operate the same as vibration member 45. The functionality of both sexual stimulation devices 25 and 125 is the same. Central ridge 118 can be positioned to the desired location by pulling upper ring 110 with the user's index finger. Similarly, lower ring 120 is designed to stretch around a male's penis and testicles.

Similar to vibrating control ring 25, vibrating control ring 125 can be separated into two major components, vibration member 145 and rubber exterior 155, by removing vibration member 145 through opening 139 in rubber exterior 155. Vibration member 145 has an upper section with a power button 130. Batteries comparable to 62A and 62 B can be inserted into a closed housing Similar to the preferred embodiment, the vibration member 145 within flexible housing 155 is used for sexual stimulation.

Figure 8:
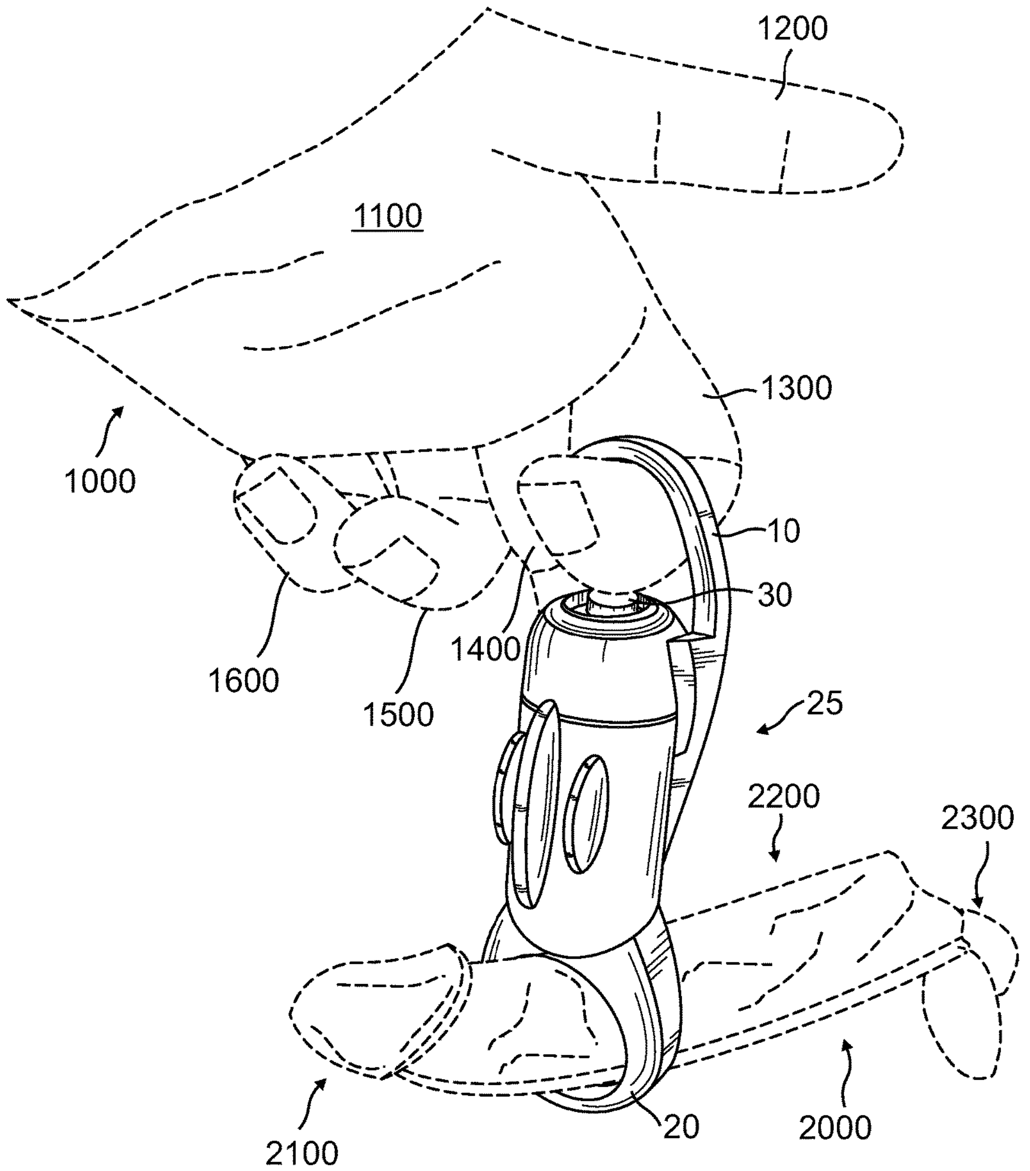
FIG. 8 is a front-side perspective view of the present invention taken from the view illustrated in FIG. 2, illustrating the ride control ring in use, the hand, fingers and penis and testicles illustrated in dashed lines.

Referring to FIG. 8, there is illustrated in dashed lines a left hand 1000 with palm 1100, thumb 1200, forefinger 1300, middle finger 1400, ring finger 1500 and pinkie 1600. There is also illustrated in dashed lines the penis 2000 including head 2100 and shaft 2200 and testicles 2300. The sexual stimulation device, also referred to as a ride control ring 25 is illustrated in use with the forefinger 1300 inserted into the upper ring and lower ring 20 stretched around the shaft 2200 and, if desired, also stretched around the testicles 2300 (stretching around testicles not illustrated). With the power button 30 pressed, the penis 2000 is stimulated by the vibrations transmitted from the vibration member 45 through the housing 55 with the penis 2000 further stimulated by one or more of the position or stimulation sensors 12, 14, 16 illustrated in FIG. 1 (or 118 illustrated in FIG. 6) pressed against the shaft 2200 or head 2100. If the woman is controlling the ride control ring 25 the woman can control when the penis is inserted in her body part such as vagina or mouth. If desired, a portion of the ride control ring 25 can also be inserted into other body parts.

It will be appreciated that the on/off button and pulse selector button can perform a multiplicity of different functions and the specific functions just identified are illustrative purposes only, and not illustrated for way of limitation. The vibration member 45 or 145 can also be referred to as a vibration motor.

Of course the present invention is not intended to be restricted to any particular form or arrangement, or any specific embodiment, or any specific use, disclosed herein, since the same may be modified in various particulars or relations without departing from the spirit or scope of the claimed invention herein above shown and described of which the apparatus or method shown is intended only for illustration and disclosure of an operative embodiment and not to show all of the various forms or modifications in which this invention might be embodied or operated.

What is claimed is:

1. A sexual stimulation device adapted for use with a finger of a first user and used in conjunction with a penis having at least a shaft and a head of a second user, the sexual stimulation device comprising:

a. a main housing member having an exterior wall with a multiplicity of spaced apart sensation ridges extending transversely to said exterior wall of said main housing member, the main housing member having a first end with a central opening surrounded by a circumferential wall, the central opening leading to an interior chamber housing a battery powered vibration member with a power button of the battery powered vibration member extending out of said central opening;

b. a first ring affixed to a portion of a back exterior of said main housing member exterior wall and a partially circumferential wall portion of the first ring extending for a distance beyond said first end and surrounding an interior opening being able to receive and adapted for use with a finger of a hand of said first user;

c. a second stretchable ring affixed to a portion of a second end of said main housing member, the second stretchable ring having sufficient elasticity to be inserted over and used in conjunction with said shaft of said penis; and d. the battery operated vibration member providing vibration forces to said main housing member after the vibration member is activated by said power button;

e. whereby said first user is able to control the penis of the second user after the second stretchable ring is positioned around said shaft of said penis of said second user and said first user has inserted a finger of said first user through said interior opening in said first ring.

2. The sexual stimulating device in accordance with claim 1, further comprising: said main housing member is made of material selected from the group consisting of rubber, polyvinyl and flexible rubberized material.

3. The sexual stimulation device in accordance with claim 1, where the second user has testicles at an end of said penis, said sexual stimulation device further comprising; said second stretchable ring is further adapted to be inserted over said testicles.

4. The sexual stimulation device in accordance with claim 1, further comprising: said multiplicity of spaced apart sensation ridges are three sensation ridges positioned on a front exterior surface of said main housing member.

5. The sexual stimulation device in accordance with claim 1, further comprising: said vibration member is operated by said power button so that depressing said power button once turns on the vibration member on, pressing said power button twice causes a low level of vibration, depressing the power button three times yields a highest vibrating speed, depressing the power button four times causes the vibration member to generate pulses, depressing the power button five times turns the vibration member off.

6. A sexual stimulation device adapted for use with a finger of a first user and used in conjunction with a penis having at least a shaft and a head of a second user, the sexual stimulation device comprising:

a. a main housing member having an exterior wall with at least one sensation ridge extending transversely to said exterior wall of said main housing member, the main housing member having a first end with a central opening leading to an interior chamber housing a powered vibration member with an activation member, powered vibration member extending out of said central opening;

b. a first flexible member affixed to a portion of a back exterior of said main housing member exterior wall and a partially circumferential wall portion of the first flexible member extending for a distance away from said main housing and surrounding an interior opening being able to receive and adapted for use with a finger of a hand of said first user;

c. a second stretchable member affixed to a portion of a second end of said main housing member, the second stretchable member having sufficient elasticity to be inserted over and used in conjunction with said shaft of said penis; and d. the powered vibration member providing vibration forces to said main housing member after the vibration member is activated by said activation member;

e. whereby said first user is able to control the penis of the second user after the second stretchable member is positioned around said shaft of said penis of said second user and said first user has inserted a finger of said first user through said interior opening in said first flexible member.

7. The sexual stimulating device in accordance with claim 6, further comprising: said main housing member is made of material selected from the group consisting of rubber, polyvinyl and flexible rubberized material.

8. The sexual stimulation device in accordance with claim 6, where the second user has testicles at an end of said penis, said sexual stimulation device further comprising; said second stretchable ring is further adapted to be inserted over said testicles.

9. The sexual stimulation device in accordance with claim 6, further comprising: said at least one sensation ridges are three sensation ridges positioned on a front exterior surface of said main housing member.

10. The sexual stimulation device in accordance with claim 6, further comprising: said powered vibration member is operated by said activation member so that depressing said activation member once turns on the powered vibration member on, pressing said activation member twice causes a low level of vibration, depressing the activation member three times yields a highest vibrating speed, depressing the activation member four times causes the powered vibration member to generate pulses, depressing activation member five times turns the vibration member off.

* * * * *